United States Patent [19]
Brake et al.

[11] Patent Number: 5,010,182
[45] Date of Patent: Apr. 23, 1991

[54] DNA CONSTRUCTS CONTAINING A KLUYVEROMYCES ALPHA FACTOR LEADER SEQUENCE FOR DIRECTING SECRETION OF HETEROLOGOUS POLYPEPTIDES

[75] Inventors: Anthony J. Brake, Berkeley, Calif.; Johan A. Van Den Berg, Ad Reeuwijk, Netherlands

[73] Assignees: Chiron Corporation, Emeryville, Calif.; Gist-Brocades NV, Delft, Netherlands

[21] Appl. No.: 78,551

[22] Filed: Jul. 28, 1987

[51] Int. Cl.$^5$ ............ C07H 15/12; C12P 21/00; C12N 15/00
[52] U.S. Cl. ............ 536/27; 435/69.1; 435/172.3; 435/255; 435/256; 435/320; 935/1; 935/28; 935/37; 935/48; 935/69
[58] Field of Search ............ 435/68, 320, 172.3, 435/255, 256; 935/22, 37, 69; 536/27

[56] References Cited

FOREIGN PATENT DOCUMENTS 0123544 10/1984 European Pat. Off. .
0171000 2/1986 European Pat. Off. .
0324274 7/1989 European Pat. Off. .

OTHER PUBLICATIONS

Fujimura, et al. *Arch. Microbiol.* 132: 225-229, 1982.
Egel-Mitani Abstract Accession # YOO385 (England) 1987 p. 6303.
Das. *J. Bacti* 158(3): 1165-1167, 1984.
Rieger, et al., *Glossary of Genetics* New York: Springer-Vrelag 1976 p. 510.
Sakurai *FEBS* 203(2); 285-288, 1986.
Yanagishima *Arch. Microbiol.* 129:281-284, 1981.
Mas, J. et al. *J. Gen. Microbiol.* 121:433-440, 1980.

*Primary Examiner*—Robin L. Teskin
*Assistant Examiner*—Beth A. Burrous
*Attorney, Agent, or Firm*—Barbara Rae-Venter

[57] ABSTRACT

DNA constructs that are useful for providing secretory expression of heterologous polypeptides in yeast comprising a DNA sequence that includes a Kluyveromyces α-factor leader sequence linked to the heterologous polypeptide by a yeast processing signal. Constructs employing the *K. lactis* α-factor leader and processing signal sequences, with and without spacer, linked to prochymosin are exemplified.

7 Claims, 17 Drawing Sheets

```
Trp Ser Trp Ile Thr Leu
TGG QZV TGG ATL ACN YTI
```

Code for ambiguous bases:

| | | | |
|---|---|---|---|
| Q: | A or T | L: | A,T, or C |
| R: | A or G | N: | any base |
| S: | A or C | V: | T or C if preceded by AG; else any base |
| Y: | T or C | I: | A or G if preceded by TT; else any base |
| Z: | C or G | P: | A or G if preceded by AG; else any base |

```
         3'                    5'
POOL #1  ACC AGG ACC TAG TGG GA
               A       A   A A
               T       T   T
               C           C

3'                    5'
POOL #2  ACC TCG ACC TAG TGG GA
               A       A   A A
                       T   T
                           C
```

FIG. 1

```
  1  CTGCAGTTTGTGAATCGTAAGACAGTGACATTTTTAGAGGTTGTTATCTGTTTAAGACGAAA
     GACGTCAAACACTTAGCATTCTGTCACTGTAAAAATCTCCAACAATAGACAAATTCTGCTTT

1 PSTI

63  TGGTTTGCTGTTCAAGCTCACTGGGTGATCGGATTTCGGGAAAATTCATATATAAAGGAC
     ACCAAACGACAAGTTCGAGTGACCCACTAGCCTAAAGCCCTTTTAAGTATATATTTCCTG

81 DRA3

123  CCTTGATTGATAGGATGTTATGGTATTGTTCTAAGTTTGTTTCAATAGTAATTTCAATAT
     GGAACTAACTATCCTACAATACCATAACAAGATTCAAACAAAGTTATCATTAAAGTTATA

183  AGTATATTAGAACAAGCAAACCAGAGCATCTAAAGCCCAACTCGTCTGATCTTTTTCTGT
     TCATATAATCTTGTTCGTTTGGTCTCGTAGATTTCGGGTTGAGCAGACTAGAAAAAGACA

243  CTTTATTATCCTGAACTTCACCTTAATCTAAATTATACAAACCCAACTATCCAATTTGAA
     GAAATAATAGGACTTGAAGTGGAATTAGATTTAATATGTTTGGGTTGATAGGTTAAACTT

MetLysPheSerThrIleLeuAlaAlaSerThrAlaLeuIleSerVal
303  CTATCCAATATTATGAAATTCTCTACTATATTAGCCGCATCTACTGCTTTAATTTCCGTT
     GATAGGTTATAATACTTTAAGAGATGATATAATCGGCGTAGATGACGAAATTAAAGGCAA

309 SSPI

ValMetAlaAlaProValSerThrGluThrAspIleAspAspLeuProIleSerValPro
363  GTTATGGCTGCTCCAGTTTCTACCGAAACTGACATCGACGATCTTCCAATTTCGGTTCCA
     CAATACCGACGAGGTCAAAGATGGCTTTGACTGTAGCTGCTAGAAGGTTAAAGCCAAGGT

GluGluAlaLeuIleGlyPheIleAspLeuThrGlyAspGluValSerLeuLeuProVal
423  GAAGAAGCCTTGATTGGATTCATTGACTTAACCGGGGATGAAGTTTCCTTGTTGCCTGTT
     CTTCTTCGGAACTAACCTAAGTAACTGAATTGGCCCCTACTTCAAAGGAACAACGGACAA

AsnAsnGlyThrHisThrGlyIleLeuPheLeuAsnThrThrIleAlaGluAlaAlaPhe
483  AATAACGGAACCCACACTGGTATTCTATTCTTAAACACCACCATCGCTGAAGCTGCTTTC
     TTATTGCCTTGGGTGTGACCATAAGATAAGAATTTGTGGTGGTAGCGACTTCGACGAAAG

492 HGIE2

AlaAspLysAspAspLeuLysLysArgGluAlaAspAlaSerProTrpSerTrpIleThr
543  GCTGACAAGGATGATTTGAAGAAAAGAGAAGCCGATGCTTCCCCATGGAGTTGGATTACT
     CGACTGTTCCTACTAAACTTCTTTTCTCTTCGGCTACGAAGGGGTACCTCAACCTAATGA

585 BSTXI, NCOI

LeuArgProGlyGlnProIlePheLysArgGluAlaAsnAlaAspAlaAsnAlaGluAla
603  CTAAGACCTGGTCAACCAATCTTTAAAAGAGAAGCCAACGCTGACGCTAATGCTGAAGCA
     GATTCTGGACCAGTTGGTTAGAAATTTTCTCTTCGGTTGCGACTGCGATTACGACTTCGT

607 TTH3I, 624 AHA3
```

```
           SerProTrpSerTrpIleThrLeuArgProGlyGlnProIlePheLysArgGluAlaAsn
663        TCCCCATGGAGCTGGATTACTCTAAGACCTGGTCAACCGATCTTTAAGAGAGAGGCTAAT
           AGGGGTACCTCGACCTAATGAGATTCTGGACCAGTTGGCTAGAAATTCTCTCTCCGATTA

666 BSTXI, NCOI, 688 TTH3I

AlaAspAlaAsnAlaAspAlaSerProTrpSerTrpIleThrLeuArgProGlyGlnPro
723        GCTGATGCCAATGCAGATGCCTCCCCATGGAGCTGGATCACTCTAAGACCTGGTCAACCA
           CGACTACGGTTACGTCTACGGAGGGGTACCTCGACCTAGTGAGATTCTGGACCAGTTGGT

747 BSTXI, NCOI, 769 TTH3I

IlePheLysArgGluAlaAsnProGluAlaGluAlaAspAlaLysProSerAlaTrpSer
783        ATCTTTAAAAGAGAAGCCAACCCTGAGGCCGAGGCTGATGCCAAACCTAGTGCTTGGAGT
           TAGAAATTTTCTCTTCGGTTGGGACTCCGGCTCCGACTACGGTTTGGATCACGAACCTCA

786 AHA3, 804 MST2

TrpIleThrLeuArgProGlyGlnProIlePheOP
843        TGGATTACATTAAGACCTGGCCAACCAATTTTCTGAATTAGAAGGAAATTGACTTTTTGA
           ACCTAATGTAATTCTGGACCGGTTGGTTAAAAGACTTAATCTTCCTTTAACTGAAAAACT

860 BALI

903        CTCGTTTTCCAATGCGTCTATCTAATTTCTTCCAAAAGACAATACCCATCTTCCTTATAC
           GAGCAAAAGGTTACGCAGATAGATTAAAGAAGGTTTTCTGTTATGGGTAGAAGGAATATG

963        TTTTTTTATTTATCCAAACGAATTC
           AAAAAAATAAATAGGTTTGCTTAAG

982 ECORI
```

```
K. lactis  Met Lys Phe Ser Thr Ile Leu Ala Ala Ser Thr Ala Leu Ile Ser Val Val Met Ala Ala Pro Val Ser Thr Glu Thr Asp
             1                           10                                  20
S. cere.   Met Arg Phe Pro Ser Ile Phe Thr Ala Val Leu Phe Ala Ala Ser Ser Ala Leu Ala Ala Pro Val Asn Thr Thr Thr Glu
             1                           10                                  20

Ile Asp Asp Leu Pro Ile Ser Val Pro Glu Glu Ala Leu Ile Gly Phe Ile Asp Leu Thr Gly Asp  -   -  Glu Val Ser Leu Leu Pro
                         30                          40                                              50
           Asp Glu Thr Ala Gln Ile  -   -  Pro Ala Glu Ala Val Ile Gly Tyr Leu Asp Leu Glu Gly Asp Phe Asp Val Ala Val Leu Pro
                         30                          40                                              50

Val Asn Asn Gly Thr His Thr Gly Ile Leu Phe Leu Asn Thr Thr Ile Ala  -  Glu Ala Ala Phe Ala Asp Lys Asp Asp Leu Lys
                         60                          70                                              80
           Phe Ser Asn Ser Thr Asn Asn Gly Leu Leu Phe Ile Asn Thr Thr Ile Ala Ser Ile Ala Ala Lys Glu Glu Gly Val Ser Leu Asp
                         60                          70                                              80

Lys Glu Ala Asp Ala Ser Pro  -   -   -   -   -   -   -   -   -  Trp Ser Trp Ile Thr Leu Arg Pro Gly Gln Pro Ile Phe
                         90                                                                        100
           Lys Arg Glu Ala Ala Glu Ala  -   -   -   -   -   -   -   -   -  Trp His Trp Leu Gln Leu Lys Pro Gly Gln Pro Met Tyr
                                                                             90                                          100

Lys Arg Glu Ala Asn Ala Asp Ala Asn Ala Glu Ala Ser Pro  -   -   -  Trp Ser Trp Ile Thr Leu Arg Pro Gly Gln Pro Ile Phe
                        110                         120                                              130
           Lys Arg Glu Ala Ala Glu Ala  -   -   -   -   -   -   -   -   -  Trp His Trp Leu Gln Leu Lys Pro Gly Gln Pro Met Tyr
                        110                                                                        120

Lys Arg Glu Ala Asn Ala Asp Ala Asn Ala Asp Ala Ser Pro  -   -   -  Trp Ser Trp Ile Thr Leu Arg Pro Gly Gln Pro Ile Phe
                        140                         150                                              160
           Lys Arg Glu Ala Ala Asp Ala Glu Ala  -   -   -   -   -   -   -  Trp His Trp Leu Gln Leu Lys Pro Gly Gln Pro Met Tyr
                        130                                                 140

Lys Arg Glu Ala Asn Pro Glu Ala Glu Ala Asp Ala Lys Pro Ser Ala Trp Ser Trp Ile Thr Leu Arg Pro Gly Gln Pro Ile Phe  187
                        170                         180
           Lys Arg Glu Ala Asp Ala Glu Ala  -   -   -   -   -   -   -   -  Trp His Trp Leu Gln Leu Lys Pro Gly Gln Pro Met Tyr  165
                        150                                                 160
```

FIG. 3

FIG.4
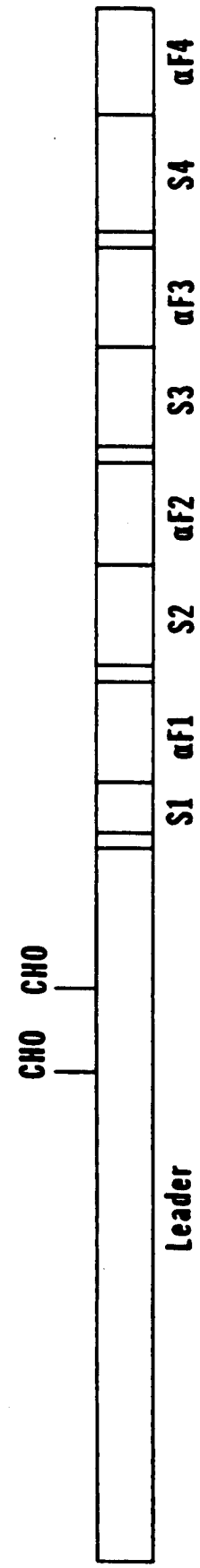
K. lactis
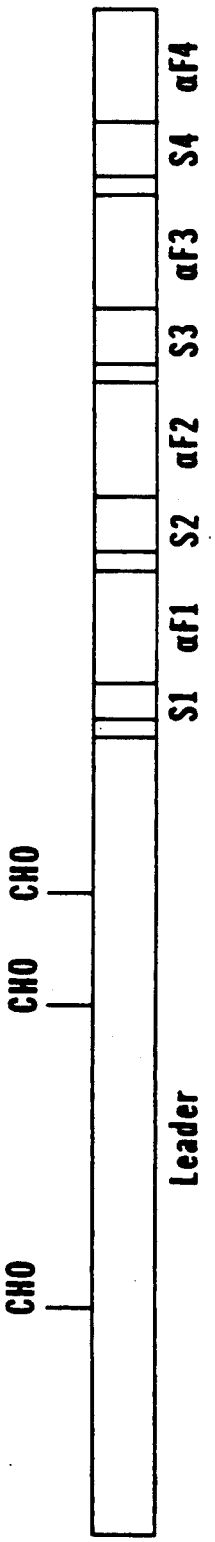
S. cerevisiae

```
K.l.  1   ATGAAATTCTCTACTATATTAGCCGCATCTACTGCTTAATTCCGTTGTTATGGCTGCTCCAGTTCTACCGAAACTGAC
S.c.  1   ATGAGATTCCTTCAATTTTACTGCAGTTTTATTCGCAGCATCCTCCGCATTAGCTGCTCCAGTCGCTCAACTACAACAGAA

82    ATCGACGATCTTCCAATTCGGTTCCAGAGAAGCCTGATTGGATTCATTGACTAACGGGAT---GAAGTTCCTGTTGCCT
82    GATGAAACGGCACAAATT------CCGGGCTGAAGCTGTGTCATCGGTTACTAGATTTAGAAGGGGATTTCGATGTTGCTGTGTTTTGCCA

166   GTTAATAACGGAACCCACACTGTATTCTATTCTTAAACACCACCATCGCT---GAAGCTGCTTCGCTGACAAGGATGATTGAAG
163   TTTTCCAACAGCACAAATAACGGGTTATTGTTTATAAATACTACTATTGCCAGCATTGCTGCTAAAGAAGAAGGGGTATCTTTGGAT

250   AAAGAGAAGCCGATGCTTCCCCA-----------------------TGGAGTTGGATTACTCTAAGACCTGTCAACCATCTTT
250   AAAGAGAGGCTGAAGCT-----------------------------TGGCATTGGTCGCAACTAAACCTGGCAACCAATGTAC

313   AAAGAGAAGCCAACGCTGACGCTAATGCTGAAGCATCCCCA-----------------TGGAGCTGGATTACTCTAAGACCTGTCAACCGATCTTT
307   AAGAGAGAAGCCGAAGCTGAAGCT------------------------------TGGCATTGGCTGCAACTAAAGCCTGCCAACCAATGTAC

394   AAGAGAGAAGCCTAATGCTGATGCCAATGCAGATGCCTCCCCA-----------------TGGAGCTGATCACTCTAAGACCTGTCAACCAATCTTT
370   AAAGAGAAGCCGACGCTGAAGCT--------------------------TGGCATTGGCCTGCAACTAAAGCCTGGCAACCAATGTAC

475   AAAGAGAAGCCAACCCTGAGCCGAGGCTGATGCCAAACCTAGTGCTTGAGTTGATTACATTAAGACCTGGCCAACCAATTTC
433   AAAGAGAAGCCGACGCTGAAGCT-----------------TGGCATTGGTTGCAGTTAAACCCGGCCAACCAATGTAC
```

FIG.5

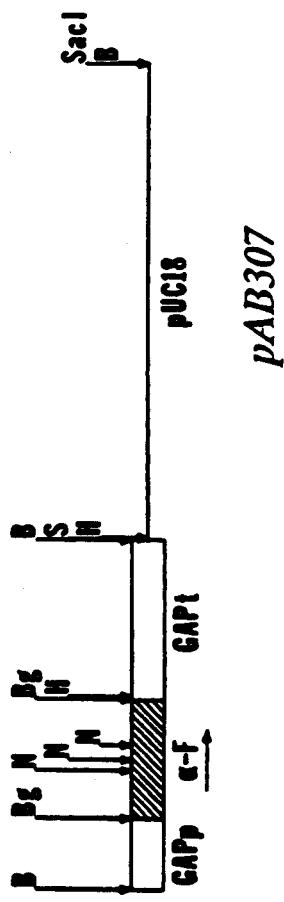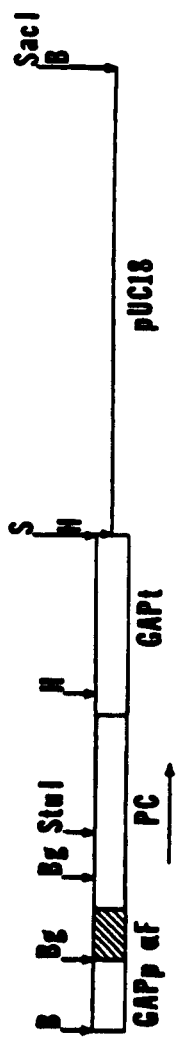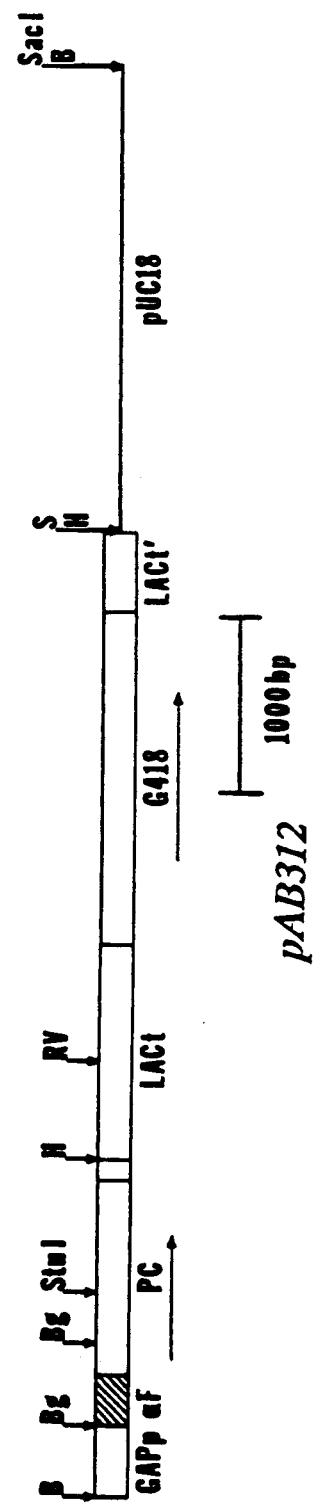
FIG.6

```
  1  GGATCCCCAGCTTAGTTCATAGGTCCATTCTCTTAGCGCAACTACAGAGAACAGGGGCAC
     CCTAGGGGTCGAATCAAGTATCCAGGTAAGAGAATCGCGTTGATGTCTCTTGTCCCCGTG
                                                                ^
     1 BAMHI,

61  AAACAGGCAAAAAACGGGCACAACCTCAATGGAGTGATGCAACCTGCCTGGAGTAAATGA
     TTTGTCCGTTTTTTGCCCGTGTTGGAGTTACCTCACTACGTTGGACGGACCTCATTTACT

121  TGACACAAGGCAATTGACCCACGCATGTATCTATCTCATTTTCTTACACCTTCTATTACC
     ACTGTGTTCCGTTAACTGGGTGCGTACATAGATAGAGTAAAAGAATGTGGAAGATAATGG

181  TTCTGCTCTCTCTGATTTGGAAAAAGCTGAAAAAAAAGGTTGAAACCAGTTCCCTGAAAT
     AAGACGAGAGAGACTAAACCTTTTTCGACTTTTTTTCCAACTTTGGTCAAGGGACTTTA
                                                              ^
     236 XMNI,

241  TATTCCCCTACTTGACTAATAAGTATATAAAGACGGTAGGTATTGATTGTAATTCTGTAA
     ATAAGGGGATGAACTGATTATTCATATATTTCTGCCATCCATAACTAACATTAAGACATT

301  ATCTATTTCTTAAACTTCTTAAATTCTACTTTTATAGTTAGTCTTTTTTTTAGTTTTAAA
     TAGATAAAGAATTTGAAGAATTTAAGATGAAAATATCAATCAGAAAAAAAATCAAAATTT
                                                                ^
     355 AHA3,

MetLysPheSer
361  ACACCAAGAACTTAGTTTCGAATAAACACACATAAACAGATCTTCATTATGAAATTCTCT
     TGTGGTTCTTGAATCAAAGCTTATTTGTGTGTATTTGTCTAGAAGTAATACTTTAAGAGA
                 ^                           ^
     377 ASU2, 398 BGL2,

ThrIleLeuAlaAlaSerThrAlaLeuIleSerValValMetAlaAlaProValSerThr
421  ACTATATTAGCCGCATCTACTGCTTTAATTTCCGTTGTTATGGCTGCTCCAGTTTCTACC
     TGATATAATCGGCGTAGATGACGAAATTAAAGGCAACAATACCGACGAGGTCAAAGATGG

GluThrAspIleAspAspLeuProIleSerValProGluGluAlaLeuIleGlyPheIle
481  GAAACTGACATCGACGATCTTCCAATTTCGGTTCCAGAAGAAGCCTTGATTGGATTCATT
     CTTTGACTGTAGCTGCTAGAAGGTTAAAGCCAAGGTCTTCTTCGGAACTAACCTAAGTAA

AspLeuThrGlyAspGluValSerLeuLeuProValAsnAsnGlyThrHisThrGlyIle
541  GACTTAACCGGGGATGAAGTTTCCTTGTTGCCTGTTAATAACGGAACCCACACTGGTATT
     CTGAATTGGCCCCTACTTCAAAGGAACAACGGACAATTATTGCCTTGGGTGTGACCATAA
                                                            ^
     586 HGIE2,
```

```
                LeuPheLeuAsnThrThrIleAlaGluAlaAlaPheAlaAspLysAspAspLeuLysLys
        601     CTATTCTTAAACACCACCATCGCTGAAGCTGCTTTCGCTGACAAGGATGATTTGAAGAAA
                GATAAGAATTTGTGGTGGTAGCGACTTCGACGAAAGCGACTGTTCCTACTAAACTTCTTT

ArgGluAlaAspAlaSerHisHisMetAlaGluIleThrArgIleProLeuTyrLysGly
        661     AGAGAAGCCGATGCTTCCCATCATATGGCTGAGATCACCAGGATCCCTCTGTACAAAGGC
                TCTCTTCGGCTACGAAGGGTAGTATACCGACTCTAGTGGTCCTAGGGAGACATGTTTCCG
                              ^       ^                ^
                678 PFLM1, 682 NDEI, 701 BAMHI,

LysSerLeuArgLysAlaLeuLysGluHisGlyLeuLeuGluAspPheLeuGlnLysGln
        721     AAGTCTCTGAGGAAGGCGCTGAAGGAGCATGGGCTTCTGGAGGACTTCCTGCAGAAACAG
                TTCAGAGACTCCTTCCGCGACTTCCTCGTACCCGAAGACCTCCTGAAGGACGTCTTTGTC
                                                                 ^
                769 PSTI,

GlnTyrGlyIleSerSerLysTyrSerGlyPheGlyGluValAlaSerValProLeuThr
        781     CAGTATGGCATCAGCAGCAAGTACTCCGGCTTCGGGGAGGTGGCCAGCGTCCCCCTGACC
                GTCATACCGTAGTCGTCGTTCATGAGGCCGAAGCCCCTCCACCGGTCGCAGGGGGACTGG
                                  ^                   ^          ^
                800 SCAI, 821 BALI, 839 BSTXI,

AsnTyrLeuAspSerGlnTyrPheGlyLysIleTyrLeuGlyThrProProGlnGluPhe
        841     AACTACCTGGACAGTCAGTACTTTGGGAAGATCTACCTCGGGACCCCGCCCCAGGAGTTC
                TTGATGGACCTGTCAGTCATGAAACCCTTCTAGATGGAGCCCTGGGGCGGGGTCCTCAAG
                                 ^              ^
                857 SCAI, 869 BGL2,

ThrValLeuPheAspThrGlySerSerAspPheTrpValProSerIleTyrCysLysSer
        901     ACCGTGCTGTTTGACACTGGCTCCTCTGACTTCTGGGTACCCTCTATCTACTGCAAGAGC
                TGGCACGACAAACTGTGACCGAGGAGACTGAAGACCCATGGGAGATAGATGACGTTCTCG
                                              ^
                936 KPNI,

AsnAlaCysLysAsnHisGlnArgPheAspProArgLysSerSerThrPheGlnAsnLeu
        961     AATGCCTGCAAAAACCACCAGCGCTTCGACCCGAGAAAGTCGTCCACCTTCCAGAACCTG
                TTACGGACGTTTTTGGTGGTCGCGAAGCTGGGCTCTTTCAGCAGGTGGAAGGTCTTGGAC
                                                                      ^^
                1011 PFLM1, 1012 ALWN1,

GlyLysProLeuSerIleHisTyrGlyThrGlySerMetGlnGlyIleLeuGlyTyrAsp
        1021    GGCAAGCCCCTGTCTATCCACTACGGGACAGGCAGCATGCAGGGCATCCTGGGCTATGAC
                CCGTTCGGGGACAGATAGGTGATGCCCTGTCCGTCGTACGTCCCGTAGGACCCGATACTG
                           ^                                     ^
                1055 SPHI, 1078 TTH3I,

ThrValThrValSerAsnIleValAspIleGlnGlnThrValGlyLeuSerThrGlnGlu
        1081    ACCGTCACTGTCTCCAACATTGTGGACATCCAGCAGACAGTAGGCCTGAGCACCCAGGAG
                TGGCAGTGACAGAGGTTGTAACACCTGTAGGTCGTCTGTCATCCGGACTCGTGGGTCCTC
                                ^                             ^
                1094 BSTXI, 1122 STUI,
```

```
         ProGlyAspValPheThrTyrAlaGluPheAspGlyIleLeuGlyMetAlaTyrProSer
1141     CCCGGGGACGTCTTCACCTATGCCGAATTCGACGGGATCCTGGGGATGGCCTACCCCTCG
         GGGCCCCTGCAGAAGTGGATACGGCTTAAGCTGCCCTAGGACCCCTACCGGATGGGGAGC
         ^     ^            ^         ^
         1141 SMAI XMAI, 1147 AAT2, 1165 ECORI, 1175 BAMHI,

LeuAlaSerGluTyrSerIleProValPheAspAsnMetMetAsnArgHisLeuValAla
1201     CTCGCCTCAGAGTACTCGATACCCGTGTTTGACAACATGATGAACAGGCACCTGGTGGCC
         GAGCGGAGTCTCATGAGCTATGGGCACAAACTGTTGTACTACTTGTCCGTGGACCACCGG
                 ^                                                ^
         1211 SCAI, 1249 DRA3,

GlnAspLeuPheSerValTyrMetAspArgAsnGlyGlnGluSerMetLeuThrLeuGly
1261     CAAGACCTGTTCTCGGTTTACATGGACAGGAATGGCCAGGAGAGCATGCTCACGCTGGGG
         GTTCTGGACAAGAGCCAAATGTACCTGTCCTTACCGGTCCTCTCGTACGAGTGCGACCCC
                                  ^          ^
         1293 BALI, 1304 SPHI,

AlaIleAspProSerTyrTyrThrGlySerLeuHisTrpValProValThrValGlnGln
1321     GCCATCGACCCGTCCTACTACACAGGGTCCCTGCATTGGGTGCCCGTGACAGTGCAGCAG
         CGGTAGCTGGGCAGGATGATGTGTCCCAGGGACGTAACCCACGGGCACTGTCACGTCGTC
                                                                     ^
         1379 SCAI,

TyrTrpGlnPheThrValAspSerValThrIleSerGlyValValValAlaCysGluGly
1381     TACTGGCAGTTCACTGTGGACAGTGTCACCATCAGCGGTGTGGTTGTGGCCTGTGAGGGT
         ATGACCGTCAAGTGACACCTGTCACAGTGGTAGTCGCCACACCAACACCGGACACTCCCA
                                           ^       ^
         1399 TTH3I, 1408 HGIE2,

GlyCysGlnAlaIleLeuAspThrGlyThrSerLysLeuValGlyProSerSerAspIle
1441     GGCTGTCAGGCCATCCTGGACACGGGCACCTCCAAGCTGGTCGGGCCCAGCAGCGACATC
         CCGACAGTCCGGTAGGACCTGTGCCCGTGGAGGTTCGACCAGCCCGGGTCGTCGCTGTAG
                                                           ^
         1483 APAI,

LeuAsnIleGlnGlnAlaIleGlyAlaThrGlnAsnGlnTyrGlyGluPheAspIleAsp
1501     CTCAACATCCAGCAGGCCATTGGAGCCACACAGAACCAGTACGGTGAGTTTGACATCGAC
         GAGTTGTAGGTCGTCCGGTAACCTCGGTGTGTCTTGGTCATGCCACTCAAACTGTAGCTG

CysAspAsnLeuSerTyrMetProThrValValPheGluIleAsnGlyLysMetTyrPro
1561     TGCGACAACCTGAGCTACATGCCCACTGTGGTCTTTGAGATCAATGGCAAAATGTACCCA
         ACGCTGTTGGACTCGATGTACGGGTGACACCAGAAACTCTAGTTACCGTTTTACATGGGT

LeuThrProSerAlaTyrThrSerGlnAspGlnGlyPheCysThrSerGlyPheGlnSer
1621     CTGACCCCCTCCGCCTATACCAGCCAGGACCAGGGCTTCTGTACCAGTGGCTTCCAGAGT
         GACTGGGGGAGGCGGATATGGTCGGTCCTGGTCCCGAAGACATGGTCACCGAAGGTCTCA
```

```
             GluAsnHisSerGlnLysTrpIleLeuGlyAspValPheIleArgGluTyrTyrSerVal
1681  GAAAATCATTCCCAGAAATGGATCCTGGGGATGTTTTCATCCGAGAGTATTACAGCGTC
      CTTTTAGTAAGGGTCTTTACCTAGGACCCCCTACAAAAGTAGGCTCTCATAATGTCGCAG
                             ^
      1700 BAMHI,

PheAspArgAlaAsnAsnLeuValGlyLeuAlaLysAlaIleOP
1741  TTTGACAGGGCCAACAACCTCGTGGGGCTGGCCAAAGCCATCTGAATCTCGACTTGGTTG
      AAACTGTCCCGGTTGTTGGAGCACCCCGACCGGTTTCGGTAGACTTAGAGCTGAACCAAC
                              ^
      1769 BALI,
1801  AACACGTTGCCAAGGCTTAAGTGAATTTACTTTAAAGTCTTGCATTTAAATAAATTTTCT
      TTGTGCAACGGTTCCGAATTCACTTAAATGAAATTTCAGAACGTAAATTTATTTAAAAGA
              ^              ^            ^
      1816 AFL2, 1831 AHA3, 1845 AHA3,

1861  TTTTATAGCTTTATGACTTAGTTTCAATTTATATACTATTTTAATGACATTTTCGATTCA
      AAAATATCGAAATACTGAATCAAAGTTAAATATATGATAAAATTACTGTAAAAGCTAAGT

1921  TTGATTGAAAGCTTTGTGTTTTTTCTTGATGCGCTATTGCATTGTTCTTGTCTTTTTCGC
      AACTAACTTTCGAAACACAAAAAAGAACTACGCGATAACGTAACAAGAACAGAAAAAGCG
                 ^
      1929 HIND3,

1981  CACATGTAATATCTGTAGTAGATACCTGATACATTGTGGATGCTGAGTGAAATTTTAGTT
      GTGTACATTATAGACATCATCTATGGACTATGTAACACCTACGACTCACTTTAAAATCAA

2041  AATAATGGAGGCGCTCTTAATAATTTTGGGGATATTGGCTTTTTTTTTAAAGTTTACAA
      TTATTACCTCCGCGAGAATTATTAAAACCCCTATAACCGAAAAAAAAAATTTCAAATGTT
                                                         ^
      2087 AHA3,

2101  ATGAATTTTTTCCGCCAGGATAACGATTCTGAAGTTACTCTTAGCGTTCCTATCGGTACA
      TACTTAAAAAAGGCGGTCCTATTGCTAAGACTTCAATGAGAATCGCAAGGATAGCCATGT
                ^
      2103 XMNI,

2161  GCCATCAAATCATGCCTATAAATCATGCCTATATTTGCGTGCAGTCAGTATCATCTACAT
      CGGTAGTTTAGTACGGATATTTAGTACGGATATAAACGCACGTCAGTCATAGTAGATGTA

2221  GAAAAAAACTCCCGCAATTTCTTATAGAATACGTTGAAAATTAAATGTACGCGCCAAGAT
      CTTTTTTTGAGGGCGTTAAAGAATATCTTATGCAACTTTTAATTTACATGCGCGGTTCTA

2281  AAGATAACATATATCTAGCTAGATGCAGTAATATACACAGATTCCCGCGGACGTGGGAAG
      TTCTATTGTATATAGATCGATCTACGTCATTATATGTGTCTAAGGGCGCCTGCACCCTTC
                                                 ^
      2325 SAC2,
```

2341  GAAAAAATTAGATAACAAAATCTGAGTGATATGGAAATTCCGCTGTATAGCTCATATCTT
      CTTTTTTAATCTATTGTTTTAGACTCACTATACCTTTAAGGCGACATATCGAGTATAGAA

2401  TCCCTTCAACACCAGAAATGTAAAAATCTTGTTACGAAGGATCTTTTTGCTAATGTTTCT
      AGGGAAGTTGTGGTCTTTACATTTTTAGAACAATGCTTCCTAGAAAAACGATTACAAAGA

2461  CGCTCAATCCTCATTTCTTCCCTACGAAGAGTCAAATCTACTTGTTTTCTGCCGGTATCA
      GCGAGTTAGGAGTAAAGAAGGGATGCTTCTCAGTTTAGATGAACAAAAGACGGCCATAGT

2521  AGATCCATATCTTCTAGTTTCACCATCAAAGTCCAATTTCTAGTATACAGTTTATGTCCC
      TCTAGGTATAGAAGATCAAAGTGGTAGTTTCAGGTTAAAGATCATATGTCAAATACAGGG
                                                       ^
      2563 SNAI XCA1,

2581  AACGTAACAGACAATCAAAATTGGAAAGGATAAGTATCCTTCAAAGAATGATTCTGCGCT
      TTGCATTGTCTGTTAGTTTTAACCTTTCCTATTCATAGGAAGTTTCTTACTAAGACGCGA

2641  GGCTCCTGAACCGCCTAATGGGAACAGAGAAGTCCAAAACGATGCTATAAGAACCAGAAA
      CCGAGGACTTGGCGGATTACCCTTGTCTCTTCAGGTTTTGCTACGATATTCTTGGTCTTT

2701  TAAAACGATAAAACCATACCAGGATCGTCGAC
      ATTTTGCTATTTTGGTATGGTCCTAGCAGCTG
                                     ^
      2727 SALI,

Primer #1: Spacer Deletion

```
5'                                      3'
  GATTTGAAGAAAAGAGCTGAGATCACCAGG
```

Primer #2: Spacer Deletion + BssHII Site

```
5'                                      3'
  GATTTGAAGAAGCGCGCTGAGATCACCAGG
            BssHII
```

FIG. 11

```
          <---α-Factor Leader--><----(Spacer)-Prochymosin------------> pAB309,   AspAspLeuLysLysArgGluAlaAspAlaSerHisHisMetAlaGluIleThrArgIle
pAB312    GATGATTTGAAGAAAAGAGAAGCCGATGCTTCCCATCATATGGCTGAGATCACCAGGATC
          CTACTAAACTTCTTTTCTCTTCGGCTACGAAGGGTAGTATACCGACTCTAGTGGTCCTAG

AspAspLeuLysLysArgAlaGluIleThrArgIleProLeuTyrLysGly
pAB313    GATGATTTGAAGAAAAGAGCTGAGATCACCAGGATCCCTCTGTACAAAGGC
          CTACTAAACTTCTTTTCTCGACTCTAGTGGTCCTAGGGAGACATGTTTCCG

AspAspLeuLysLysArgAlaGluIleThrArgIleProLeuTyrLysGly
pAB314    GATGATTTGAAGAAGCGCGCTGAGATCACCAGGATCCCTCTGTACAAAGGC
          CTACTAAACTTCTTCGCGCGACTCTAGTGGTCCTAGGGAGACATGTTTCCG
                        BssHII
```

FIG. 12

DNA CONSTRUCTS CONTAINING A KLUYVEROMYCES ALPHA FACTOR LEADER SEQUENCE FOR DIRECTING SECRETION OF HETEROLOGOUS POLYPEPTIDES

TECHNICAL FIELD

This invention is in the field of recombinant DNA technology. More particularly it relates to the use of Kluyveromyces α-factor leader sequences to direct the secretion of heterologous polypeptides in yeast.

BACKGROUND

U.S. Pat. No. 4,546,082 describes the α-factor precursor gene of *Saccharomyces cerevisiae* and purports to show DNA constructs of the *S. cerevisiae* leader sequence and heterologous genes that are useful for the secretory expression of the heterologous genes. EPA 0 116 201 describes the actual use of the *S. cerevisiae* α-factor leader sequence to obtain secretory expression of human epidermal growth factor in yeast. Copending U.S. patent application Ser. No. 522,909, filed 12 August 1983, which is, in part, commonly owned with the present application, describes the use of "spacer-less" *S. cerevisiae* α-factor leader sequences to obtain more efficient secretory expression of heterologous genes.

Science (1985) 229;1219-1224 reports the use of *S. cerevisiae* α-factor sequences to direct the secretion of prochymosin. It was reported that most of the prochymosin produced was present in an intracellular insoluble form rather than being secreted. Although the invertase leader was more effective at directing secretion of activatable prochymosin, an extensive mutant screen was necessary to yield reasonable amounts of prochymosin secretion.

There has been no previous demonstration of the production of mating pheromones (α-factor and a-factor) by *Kluyveromyces lactis* cells or other Kluyveromyces species. This failure to identify such peptides in *K. lactis* may, in part, be due to the fact that mating in *K. lactis* is inducible; whereas in *S. cerevisiae* the mating pheromones are produced constitutively.

Notwithstanding the availability of the mentioned leader sequences for directing secretion of heterologous polypeptides in yeast, there continues to be a need for alternative sequences that may afford more efficient or more practical production of particular polypeptides. Accordingly, applicants sought to determine whether a *K. lactis* α-factor exists and, if so, whether it might be useful for directing secretion of heterologous polypeptides, such as prochymosin, in yeast.

DISCLOSURE OF THE INVENTION

This invention provides DNA constructs based on the Kluyveromyces α-factor leader sequence for directing the secretion of heterologous polypeptides in yeast. Kluyveromyces transformants containing these constructs provide efficient secretion of polypeptides such as prochymosin.

Accordingly one aspect of the invention is a DNA construct encoding a protein whose amino acid sequence comprises a secretion-directing Kluyveromyces α-factor leader sequence linked to a heterologous polypeptide sequence via yeast processing signals for processing said protein into the heterologous polypeptide.

Another aspect of the invention is an expression vector comprising a replicative or integrative system for providing stable maintenance in yeast functional in a yeast host and a DNA construct encoding a protein whose amino acid sequence comprises a secretion-directing Kluyveromyces α-factor leader sequence linked to a heterologous polypeptide sequence via a yeast processing signal for processing said protein into said heterologous polypeptide.

Still another aspect of the invention is a method for producing a heterologous polypeptide in yeast comprising growing yeast containing the expression vector as above in culture medium under conditions whereby said heterologous polypeptide is expressed in and secreted by said yeast as a "propolypeptide" and the polypeptide is at least partially processed into said heterologous polypeptide.

BRIEF DESCRIPTION OF THE DRAWINGS

FIG. 1 shows the strategy used to design oligonucleotide probes used to identify *K. lactis* α-factor DNA.

FIG. 2 is the complete sequence of a DNA fragment encoding the *K. lactis* α-factor.

FIG. 3 is a comparison of the protein sequences of *K. lactis* and *S. cerevisiae* α-factors.

FIG. 4 is a schematic representation of *K. lactis* and *S. cerevisiae* α-factors.

FIG. 5 is a comparison of the DNA sequences of genes encoding the *K. lactis* and *S. cerevisiae* α-factors.

FIG. 6 is a schematic representation of three plasmids whose constructions are described in detail in the examples.

FIG. 8 represents the sequence of pAB309 BamHI/-SalI insert in pUC18.

FIG. 11 represents the sequences of the primers used for mutagenesis of *K. lactis* α-factor leader DNA.

FIG. 12 represents the DNA sequences around the junctions in *K. lactis* α-factor leader/prochymosin DNA fusions.

MODES FOR CARRYING OUT THE INVENTION

Figure 7:
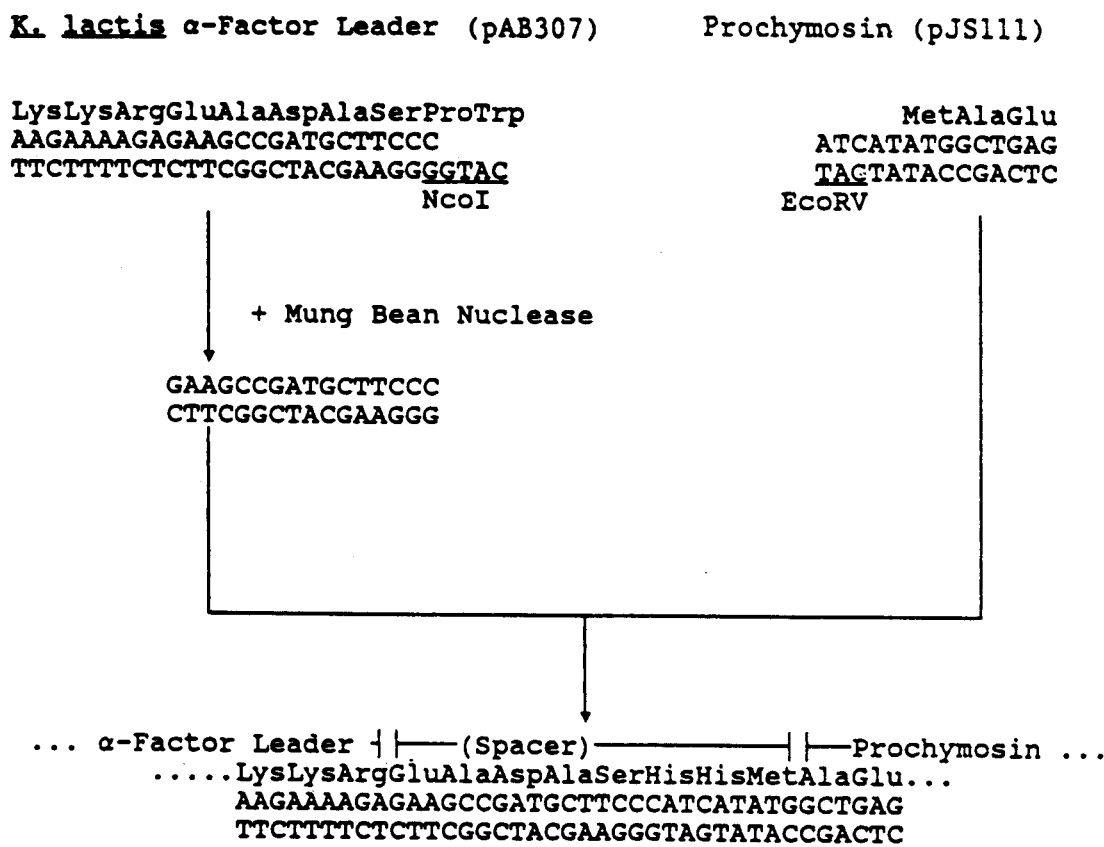
FIG. 7 is a reaction scheme showing linkage of DNA for *K. lactis* α-factor leader to DNA for prochymosin.

In accordance with the subject invention, yeast cells are employed for the production of mature heterologous polypeptides, where such polypeptides may be harvested directly from a nutrient medium. The polypeptides are produced by employing a DNA construct coding for a Kluyveromyces α-factor leader and processing signal sequence joined to the heterologous polypeptide of interest, which may be a single heterologous polypeptide or a plurality of heterologous polypeptides separated by processing signals. The resulting construct encodes a prepropolypeptide which will contain the signals for secretion of the prepropolypeptide and processing of the polypeptide, either intracellularly or extracellularly, to the mature polypeptide.

The constructs of the subject invention will comprise a DNA sequence having the following formula encoding a propolypeptide:

$$(XY-(ZW)_n-Gene^*)_y$$

wherein:

X is a codon for lysine or arginine;
Y is a codon for arginine;
W is a codon for alanine or proline;

Z is a codon for an amino acid, preferably a codon for serine, lysine or asparagine when W encodes proline and a codon for glutamic acid, asparagine, aspartic acid, or serine when W encodes alanine;

y is an integer of at least one and usually not more than 10, more usually not more than four, providing for monomers and multimers;

Gene* is a gene other than the wild type Kluyveromyces α-factor associated with the leader sequence that is foreign to a yeast host, usually a plant or mammalian gene;

n is 0 or an integer which will generally vary from 1 to 8, usually 3 to 7. preferably n is 0.

In this formula, the amino acids encoded by X, Y, Z, and W define the α-factor processing signal in which the amino acids encoded by X and Y define a dipeptide cleavage site and those encoded by Z and W define an oligopeptide spacer. As indicated by the fact that n can be zero, the spacer is optional. If a spacer is present, the construct will typically include additional sequences that allow the removal of N-terminal residues defined by the spacer to provide the mature protein encoded by Gene*

For the most part, the constructs of the subject invention will have at least the following formula:

$$L—(XY—(ZW)_n—Gene^*)_y$$

encoding a prepropolypeptide, wherein L is a Kluyveromyces leader sequence providing for secretion of the prepropolypeptide and the other symbols are as defined above. Any Kluyveromyces leader sequence may be employed which provides for secretion, leader sequences generally being of about 20 to 120 amino acids, usually about 30 to 100 amino acids, having a hydrophobic region and having a methionine at its N-terminus.

The leader sequence. L. may be a full length α-factor leader sequence of any species of Kluyveromyces, such as *K. lactis* and *K. fracilis*, or a functional (i.e., capable of directing secretion) fragment, mutation, either conservative or non-conservative, usually not more than 5, more usually not more than 3 different amino acids, or analogs thereof. Functional fragments may be identified by preparing constructs having various lengths of the wild type full length sequence and screening them for their ability to direct secretion. The gene sequence for the wild type *K. lactis* α-factor is set forth in FIG. 2 with the leader sequence being the DNA encoding amino acids 1-83. The DNA sequence of FIG. 2 is not essential. Any sequence which codes for a functional Kluyveromyces leader oligopeptide is sufficient. Different sequences will be more or less efficiently translated. Desirably, at least a majority of yeast preferred codons are employed in the sequence.

In providing for useful DNA sequences which can be used as cassettes for expression, the following sequence can be conveniently employed:

$$Tr—L—(XY—(ZW)_n—(Gene^*)_d)_y$$

wherein:

Tr intends a DNA sequence encoding for the transcriptional regulatory signals, particularly the promoter and such other regulatory signals as operators. activators, cap signal, or other sequence involved with transcriptional or translational control;

d is 0 or 1, being 1 when y is greater than 1;

The Tr sequence will generally be at least about 100 bp and not more than about 2000 bp. particularly useful is employing the Tr sequence associated with the leader sequence L, so that a DNA fragment can be employed which includes the transcriptional and translational signal sequences associated with the signal sequence endogenous to the host. Alternatively, one may employ other transcriptional and translational signals to provide for enhanced production of the expression product.

The remaining symbols have been defined previously.

The 3'-terminus of Gene* can be manipulated much more easily in the form of a construct which allows for insertion of Gene* into a unique restriction site in the construct. Such a preferred construct would provide for a restriction site with insertion of the Gene* into the restriction site to be in frame with the initiation codon. Such a construction can be symbolized as follows:

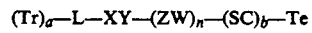

$$(Tr)_a—L—XY—(ZW)_n—(SC)_b—Te$$

wherein:

those symbols previously defined have the same definition;

a is 0 or 1 intending that the construct may or may not have the transcriptional and translational signals;

SC represents a stop codon;

Te is a transcriptional termination sequence and may include other signals, e.g., polyadenylation; and b is an integer which will generally vary from about 0 to 4, more usually from 0 to 3. it being understood that Gene* may include its own stop codon.

The sequence upstream from Gene may be designed to provide convenient restriction sites to permit a given species of Gene* to be replaced with another species of Gene*. Linkers and adapters may be used, as required, to achieve such replacement.

The construct provides a portable sequence for insertion into vectors, which provide the desired replication system. As already indicated, in some instances it may be desirable to replace the wild-type promoter associated with the signal sequence with a different promoter. In yeast, promoters involved with enzymes in the glycolytic pathway can provide for high rates of transcription. These promoters are associated with such enzymes as phosphoglucoisomerase, phosphofructokinase, phosphotriose isomerase, phosphoglucomutase, enolase, pyruvic kinase, glyceraldehyde-3-phosphate dehydrogenase, and alcohol dehydrogenase. These promoters may be inserted upstream from the signal sequence. The 5'-flanking region to the leader sequence may be retained or replaced with the 3' sequence of the alternative promoter. Vectors can be prepared and have been reported which include promoters having convenient restriction sites downstream from the promoter for insertion of such constructs as described above.

The final expression vector will comprise the expression cassette and a replicative or integrative system that is functional in and provides stable maintenance in the yeast host. The vector may optionally contain a replication system that allows for cloning in a prokaryote. In addition, one or more markers for selection will be included, which will allow for selective pressure for maintenance in the host. Furthermore, the vector may be a high or low copy number, the copy number generally ranging from about 1 to 200. With high-copy-number vectors, there will generally be at least 10, preferably at least 20 and usually not exceeding about 150, more usually not exceeding about 100, copy number. Depending upon the Gene*, either high or low copy numbers may be desirable, depending upon the effect of the vector on the host. Where the presence of the expression product of the vector may have a deleterious effect on the viability of the host, a low copy number may be indicated.

Various hosts may be employed, particularly mutants having desired properties. It should be appreciated that depending upon the rate of production of the expression product of the construct, the processing enzyme may or may not be adequate for processing at that level of production. Therefore, a mutant having enhanced production of the processing enzyme (Dipeptidyl Amino peptidase A and/or the lys-arg endopeptidase) may be indicated or enhanced production of the enzyme may be provided by means of a vector. Generally, the production of the enzyme should be of a lower order than the production of the desired expression product.

Alternatively, there may be situations where intracellular processing is not desired. In this situation, it would be useful to have a mutant, where secretion occurs, but the product is not processed. In this manner, the product may be subsequently processed in vitro.

Host mutants which provide for controlled regulation of expression may he employed to advantage. For example, with the constructions of the subject invention where a fused protein is expressed, the transformants have slow growth which appears to be a result of toxicity of the fused protein. Thus, by inhibiting expression during growth, the host may be grown to high density before changing the conditions to permissive conditions for expression.

Furthermore, as already indicated, Gene* may have a plurality of sequences in tandem, either the same or different sequences, with intervening processing signals. In this manner, the product may be processed in whole or in part, with the result that one will obtain the various sequences either by themselves or in tandem for subsequent processing. In many situations, it may be desirable to provide for different sequences, where each of the sequences is a subunit of a particular protein product.

Gene* may encode any type of polypeptide of interest. The polypeptide may be as small as an oligopeptide of 8 amino acids or may be 100,000 daltons or higher. Usually, single chains will be less than about 300,000 daltons, more usually less than about 150,000 daltons. Of particular interest are polypeptides of from about 5,000 to 150,000 daltons. more particularly of about 5,000 to 100,000 daltons. Illustrative polypeptides of interest include hormones and factors, such as growth hormone, somatomedins, and epidermal growth factor; the endocrine secretions, such as luteinizing hormone, thyroid stimulating hormone, oxytocin, insulin, vasopressin, renin, calcitonin, follicle stimulating hormone, prolactin, etc.; hematopoietic factors, e.g., erythropoietin, colony stimulating factor, etc.; lymphokines; globins; globulins, e.g., immunoglobulins; albumins: interferons, such as $\alpha$, $\beta$ and $\delta$; repressors; enzymes; endorphines e.g., $\beta$-endorphin, encephalin, dynorphin, etc.

Having prepared the vectors containing the constructs of this invention, one may then introduce them into the yeast host. The genus and species of yeast is not critical. Examples of yeast hosts are Kluyveromyces and Saccharomyces. The manner of introduction is conventional, there being a wide variety of ways to introduce DNA into the yeast host. See, for example, Hinnen et al., pNAS USA (1978) 75:1919–1933 or Das, Sunil, et al., J. Bacteriol. (1984) 158:1165–1167 or Stinchcomb et al., EPA 0 045 573. The resulting transformants may then be grown in an appropriate nutrient medium, where appropriate maintaining selective pressure on the transformants. Where expression is inducible, one can allow for growth of the yeast to high density and then induce expression. In those situations, where a substantial proportion of the product may be retained in the periplasmic space, one can release the product by treating the yeast cells with an enzyme such as zymolase or lyticase.

The product may be harvested by any convenient means, including purifying the protein by chromatography, electrophoresis, dialysis, solvent-solvent extraction, etc.

The following procedure can be carried out in order to obtain genes coding for $\alpha$-factors from Kluyveromyces species and strains other than the K. lactis strain exemplified below. A radioactively labelled oligonucleotide probe having either of the structures set forth in FIG. 1 is prepared and used to probe digests of genomic DNA from the other strain. Alternatively a nick translated fragment of the K. lactis $\alpha$-factor gene could be used as a probe. One useful technique is to insert segments from a limited endonuclease digest of genomic DNA into plasmids and to use these plasmids to transform E. coli or another bacterial strain so as to obtain a plasmid library. DNA from the colonies can then be conveniently hybridized to the probe on the nitrocellulose filters.

DNA segments identified by hybridization to the probes identified above are then digested with a variety of restriction enzymes and the resulting fragments analyzed by Southern blot or similar analysis method using the same hybridization probes in order to identify restriction fragments of a size suitable for DNA sequence analysis. Identified fragments are then purified and cloned using appropriate vectors in order that sufficient DNA can be prepared for a DNA sequence analysis.

Using these techniques, Kluyveromyces $\alpha$-factor genes can be obtained from strains other than those specifically identified herein.

In accordance with the subject invention, one can provide for secretion of a wide variety of polypeptides, so as to greatly enhance product yield, simplify purification, minimize degradation of the desired product, and simplify processing, equipment, and engineering requirements. Furthermore, utilization of nutrients based on productivity can be greatly enhanced, so that more economical and more efficient production of polypeptides may be achieved. Also, the use of yeast has many advantages in avoiding endotoxins, which may be present with prokaryotes, and employing known techniques, which have been developed for yeast over long periods of time which techniques include isolation of yeast products.

The following examples further illustrate the invention. These examples are not intended to limit the scope of the invention in any manner.

EXAMPLES

Identification and Isolation of *K. lactis* α-factor carried out as described in Julius et al. (1983) *Cell* 32. 839, using as a tester strain the *S. cerevisiae* Mat a sst2-3 strain RC687. *K. lactis* strain CBS141(α) was grown in a medium consisting of 0.5% glucose. 0.17% yeast nitrogen base without ammonium sulfate (Difco). 0.002% ammonium sulfate. After removal of cells by centrifugation, acetic acid was added to the culture supernatant to a concentration of 0.1M, and the culture supernatant was passed over a column of BioRex 70 (Biorad). The column was washed with 0.1M acetic acid. and then the α-factor was eluted with 80% EtOH/10 mM HCl. The eluate was evaporated to dryness and then dissolved in 0.1% TFA/20% acetonitrile and applied to a reverse-phase HpLC guard column. The column was washed stepwise with solutions containing 0.1% TFA and 20%, 40%. 60%. and 80% acetonitrile. The 60% fraction, containing the α-factor activity, was then applied to an analytical C-18 HPLC column and eluted with a gradient of 20% to 80% acetonitrile in 0.1% TFA. Fractions were collected and assayed for α-factor activity. The fractions containing α-factor were dried and subjected to amino acid sequence analysis using Applied Biosystems gas phase protein sequencer Model 470A coupled to a Model 120A PTH analyzer.

Hybridization Screening of plasmid Libraries

Pools of oligonucleotides were labelled using $\gamma[^{32}P]$-ATP and T4 polynucleotide kinase. These oligonucleotide probes were used to probe Southern blots or bacterial colonies at 42° C. in the following hybridization solution:

4×SSC, 50 mM $KH_2PO_4$ pH 7, 1% sarkosyl, 10% dextran sulfate, 200 μg/ml of sonicated, denatured salmon sperm DNA. Filters were washed in 2×SSC, 0.1% SDS at 42° C.

A plasmid library in the cloning vector pJS109 (other standard cloning vectors such as pUC18 and pBR322 may be used in place of pJS109), containing inserts resulting from a limited Sau3AI digest of genomic DNA from *K. lactis* strain SD11 (a trpl lac4), size-fractionated to purify fragments >5000 bp, was screened with these probes by plating transformants of *E. coli* strain HB101 at density of 500-2000 colonies per 80 mm plate of L-agar containing 100 μg/ml ampicillin. DNA was transferred from the colonies to nitrocellulose filters and these filters hybridized as described above. Areas on the original plates corresponding to regions of hybridization signals on the filters were picked and replated and then retested by hybridization to isolate single colonies with plasmids containing hybridizing sequences, positive colonies were further tested by Southern blot analysis of DNA purified from small cultures.

Plasmids purified from hybridization-positive colonies were digested with a variety of restriction enzymes and the resulting fragments analyzed by Southern blot analysis using the same hybridization probes in order to identify restriction fragments of size suitable for DNA sequence analysis. Fragments thus identified were purified by agarose gel electrophoresis and cloned into appropriate Mp18 and Mp19 vectors and DNA sequence analysis was performed.

Chymosin Assays of Culture Supernatants

Cells were removed from cultures by centrifugation, and the resulting supernatants were acidified to pH 2 by the addition of 1M $H_2SO_4$ and incubated for 2 hours at room temperature. The solutions were then neutralized to pH 6 by the addition of 2M Tris base. A 50 μl volume of an appropriate non-fat dry milk in 10 mM $CaCl_2$ and incubated at 37° C. until a clot formed. A unit of chymosin activity is defined as the amount of active chymosin required to produce a clot in 10 min under these conditions.

Results

The first 10 amino acids of the *K. lactis* α-factor showed a definite homology to that from *S. cerevisiae*, with 6 identical residues. This sequence is shown below:

Trp—Ser—Trp—Ile—Thr—Leu—Arg—Pro—Gly—Gln.

This protein sequence was used to design a set of oligonucleotides deduced to be complementary to the structural gene as shown in FIG. 1. Oligonucleotides including all of the possible codons for a segment of the α-factor peptide were synthesized as two pools of 96 and 48 different molecules.

These two pools were radioactively labelled using $\gamma[^{32}P]$-ATP and T4 polynucleotide kinase and were each used to probe a Southern blot of a restriction digest of *K. lactis* DNA. pool 2 was found to give strong hybridization to a single fragment in several different digests. Thus, pool 2 was chosen to screen plasmid libraries of *K. lactis* genomic DNA.

Use of these probes to screen plasmid libraries resulted in the isolation of a number of hybridizing clones. DNA sequence analysis of one of these clones, αfk18b, showed it to encode an α-factor-related peptide which bore a strong similarity to the precursor of the *S. cerevisiae* α-factor peptide. The hybridizing segment was found to be on a PstI-EcoRI fragment of about 1000 bp. The sequence of this fragment is shown in FIG. 2.

Comparison of the deduced α-factor precursors of this fragment is shown in FIGS. 3 and 4. As can be seen they have leader sequences of (amino acids 1-83 in FIG. 3) identical length with considerable sequence homology. The *K. lactis* precursor, however, contains only two sites for the addition of N-linked carbohydrate chains (FIG. 4). In addition, the spacers of the *K. lactis* repeats are longer than those of the *S. cerevisiae* repeats and show a more diverse sequence with the pattern X-Ala/pro rather than the Glu/Asp-Ala sequences found in *S. cerevisiae*. A comparison of the DNA sequences (FIG. 5) also shows a strong degree of homology throughout the coding region.

A series of plasmids shown in FIG. 6 were constructed in order to provide a fusion of the *K. lactis* α-factor leader to prochymosin expressed under the transcriptional control of a strong promoter. First, a 673 bp SspI-EcoRI fragment from α(klBb was modified by filling the EcoRI overhang by Klenow enzyme and addition of BglII linkers to the blunt ends. This fragment was then inserted into a BglII site joining the promoter and terminator regions of the *S. cerevisiae* glyceraldehyde-3-phosphate dehydrogenase gene (GAP). This cassette was cloned as a BamHI fragment in pUC18, resulting in pAB307.

Fusion of sequences encoding the α-leader and bovine prochymosin was then performed. First pAB307 was digested with NcoI and the cohesive ends made blunt by treatment with mung bean nuclease. The resulting product was then digested with SalI. To this was ligated a 2000 bp EcoRV-SalI fragment (sequences shown in FIG. 7 and 8) containing sequences encoding prochymosin and the *S. cerevisiae* GAP transcriptional termination region. This fragment was derived from plasmid pJS111 in which a XbaI-BamHI adaptor had been added to the 5' end of a fragment containing prochymosin cDNA fused to the *S. cerevisiae* GAP transcriptional termination region. This ligation mixture was used to transform *E. coli* strain HB101 and a transformant carrying the plasmid pAB309 was isolated. The sequences around the junction of this fusion are shown in FIG. 7, and the sequence of the entire BamHI-SalI insert of pAB309 is shown in FIG. 8.

In order to allow for transformation of *K. lactis* strains. a 3560 bp HindIII fragment containing the *E. coli* kanamycin resistance gene under the transcriptional control of the *S. cerevisiae* ADHI promoter inserted within the 3' region of the *K. lactis* LAC4 gene was inserted into pAB309 to result in the plasmid pAB312. Screening for the insert was effected by restriction digest analysis and checked for the correct orientation.

Figure 9:
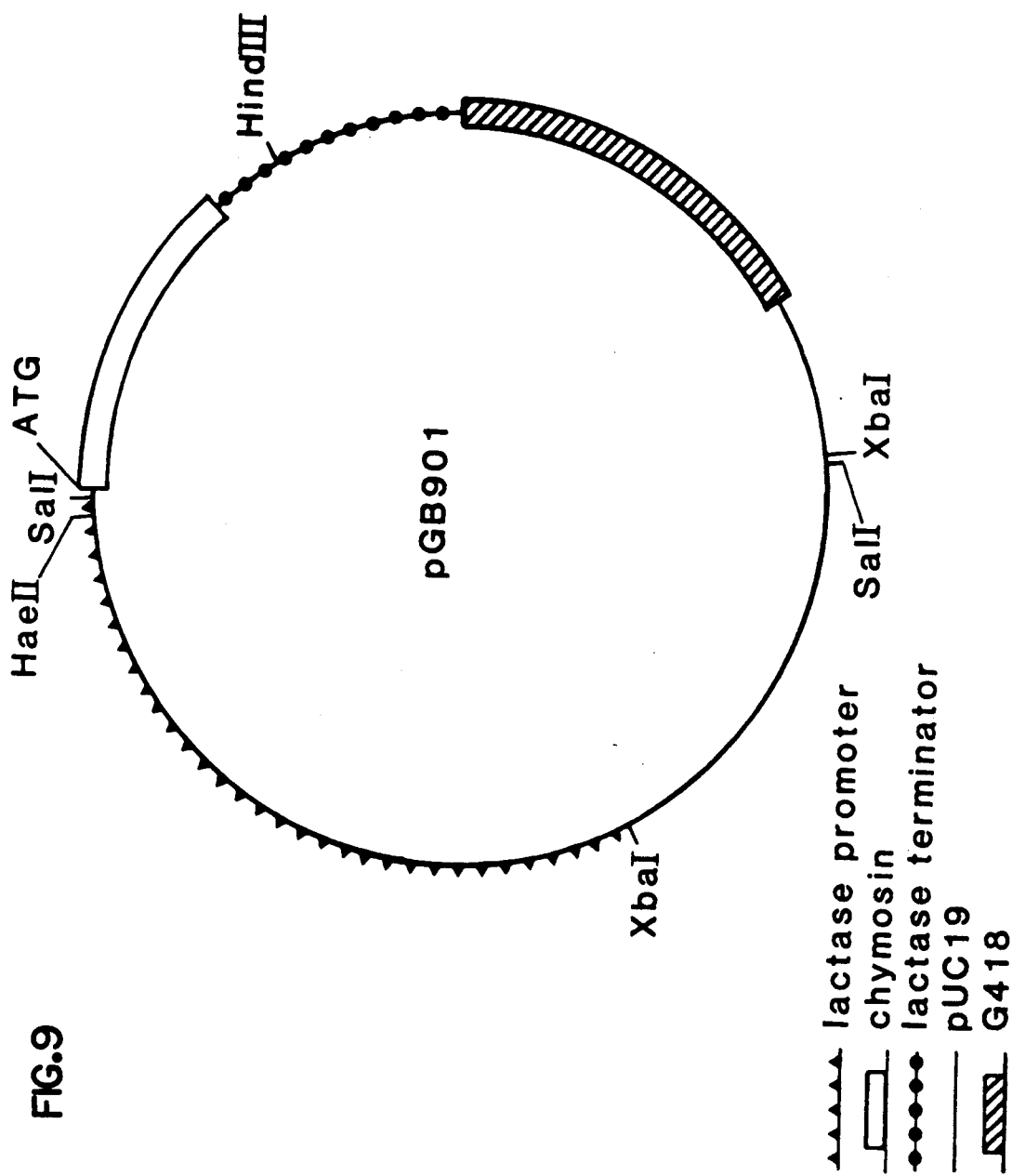
FIG. 9 is a diagram of the plasmid pGB901.

The 3560 bp HindIII fragment was derived from the plasmid pGB901, a diagram of which is shown in FIG. 9. Plasmid pGB901 was constructed by ligating (1) 3.6 kb XbaI-HaeII fragment containing the lactase promoter to about position -90 from the lactase ATG start codon isolated from pUCla56 (described below), (2) an HaeII-SalI fragment having the following nucleotide sequence

```
TTAAC ACTTGAAATT TAGGAAAGAG CAGAATTTGG CAAAAAAAAT AAAAAAAAAA TAAACACG
CGCGAATTG TGAACTTTAA ATCCTTTCTC GTCTTAAACC GTTTTTTTTA TTTTTTTTTT ATTTGTGCAG CT
```

(3) a 5.1 kb SalI-XbaI fragment encoding prochymosin and a gene conferring resistance to the antibiotic G418 from pGB900 (described below), and (4) pUC19 cleaved with XbaI.

During the construction of the plasmid the CG sequence from the HaeII site was inadvertently removed, thereby creating a HindIII site at this position.

Plasmid pUCla56 was constructed as follows. Chromosomal DNA was isolated from *K. lactis* strain CBS2360, cleaved with XhoI, and separated according to size on a sucrose gradient Fractions containing the lactase gene were detected with a LAC4 probe after spotting the DNA on a nitrocellulose filter. DNA containing the LAC4 gene was cloned into the XhoI site of plasmid ppA153-215 (p.M. Andreoli, Mol. Gen. Gen. 199 (1985) 372-380) giving rise to plasmid ppA31. An XbaI fragment of ppA31 containing the lactase gene was subcloned in the XbaI site of pUC19 (Yanisch-perron et al., Gene 33 (1985) 103-119) which yields plasmid pUCla56.

Figure 10:
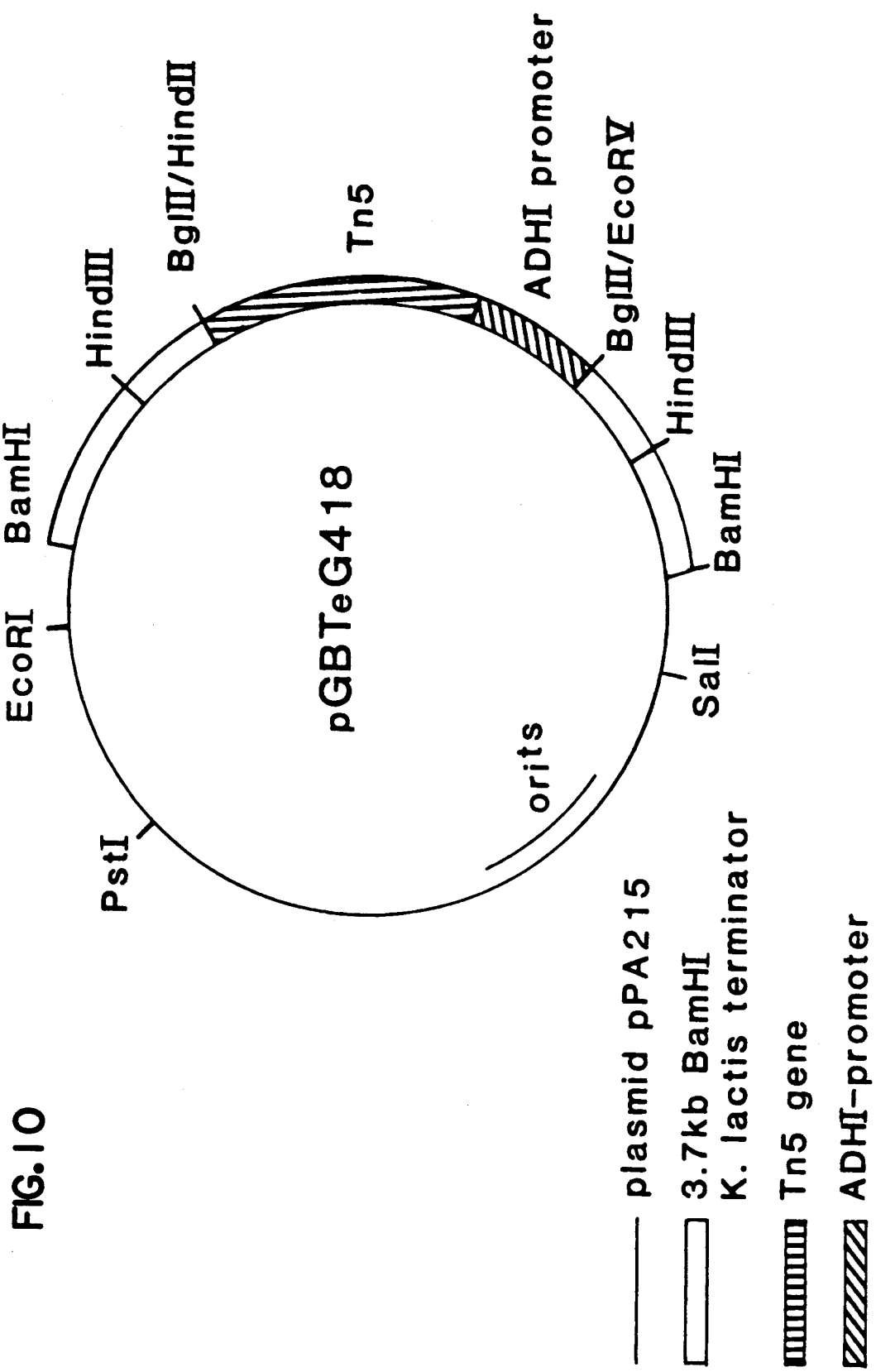
FIG. 10 is a diagram of the plasmid pGBTeG418.

Plasmid pGB900 was constructed by ligating (1) a 3.6 kb HindIII-XbaI fragment from plasmid pGBTeG418 (shown in FIG. 10 and described below) containing the G418 resistance gene and (2) a SalI-HindIII fragment from plasmid pGB123 containing the prochymosin gene in pUC19 cleaved with SalI and XbaI. Plasmid pGB123 is described in European patent application EPA 0 096 430.

pGBTeG418 (FIG. 10) consists of the plasmid pPA215 as described by Andreoli, Mol. Gen. Gen. 199 (1985) 372-380, and a 5.6 kb fragment consisting of the 3.7 kb BamHI *K. lactis* lactase terminator fragment (Breunig et al., Nucl. Ac. Res. 12 (1984) 2327-2341) and the Tn5 gene (Reiss et al., EMBO J. 3 (1984) 3317-3322) conferring resistance to gentamycin G418 under the direction of the promoter alcohol dehydrogenase I (ADHI) from yeast, similar to that as described by Bennetzen and Hall, J. Biol. Chem. 257 (1982) 3018-3025. Plasmid pGBTeG418 was deposited with CBS on 26 February 1987 under number CBS 184.87.

Plasmid pAB312 was digested with EcoRV (to target integration to the LAC4 region of the *K. lactis* genome) and was then used to transform *K. lactis* strain 2UV21 (a ura3 trp1 lac4 [kil*]) to G418 resistance using the LiCl technique described by Das et al., J. Bacteriol. 158 (1984) 1165-1167.

A number of these transformants, as well as an untransformed control strain, were grown for 36 hr in 1 ml of medium composed of 1% yeast extract, 2% peptone, 2% glucose, 0.17% yeast nitrogen base, 50 μg/ml tryptophan and 50 μg/ml uracil. Culture supernatants were then assayed for chymosin activity after acid activation. All of the transformants were found to secrete between 100 and 120 units/ml of activatable chymosin.

Removal of Spacer Codons by In Vitro Mutagenesis

A 1900 bp SacI-HindIII fragment was isolated from pAB309 and cloned into Mp19 (Yanisch-perron et al., Gene 33 (1985) 103). Single-stranded phage DNA was prepared and used as template for in vitro mutagenesis with the oligonucleotide primers shown in FIG. 11. The M13 phage MP19/ck11.5 and MP19/ck12.2 were prepared using primer #1 and primer #2, respectively.

Double-stranded RF DNA was prepared from these phage, and 1100 bp SacI-StuI fragments isolated from each. These fragments were ligated to a 7100 bp SacI-StuI fragment from pAB312. The resulting plasmids pAB313 and pAB314 were isolated with the sequence alterations illustrated in FIG. 12.

The plasmids pAB313 and pAB314 were used to transform strain 2UV21 to G418 resistance. Cultures of transformants 2UV21::pAB312, 2UV21::pAB313 and 2UV21::pAB314 were grown and culture supernatants assayed for chymosin activity as above. The results of these assays are reported in Table 1, below.

TABLE 1

| Strain | Host | Plasmid | Chymosin Activity (units/ml culture) |
|---|---|---|---|
| 2UV21 | 2UV21 | — | <2 |
| KRN303-1 | 2UV21 | pAB312 | 256 |
| KRN304-4 | 2UV21 | pAB313 | 175 |
| KRN305-2 | 2UV21 | pAB314 | 206 |

Each of the transformants was found to secrete a single prochymosin-related species as judged by SDS polyacrylamide gel electrophoresis of trichloroacetic acid-precipitated culture supernatants. The prochymosin-related protein secreted by pAB312 transformants appeared to be of slightly higher molecular weight than those secreted by pAB313 and pAB314 transformants as determined by electrophoretic mobility The cell pellets from the above strains were analyzed for chymosin activity and found to contain less than 2% of the activity measured in the supernatants. Thus the Kluyveromyces α-factor is approximately 98% efficient in directing the secretion of prochymosin from *Kluyveromyces lactis*.

The major species secreted by KRN303-1 and KRN304-4 were purified by preparative SDS polyacrylamide gel electrophoresis and subjected to gas phase amino acid sequence analysis. The N-terminal sequences of these species are given below.

KRN303-1

1          5              10              15
Glu—Ala—Asp—Ala—Ser—His—His—Met—Ala—Glu—Ile—Thr—Arg—Ile—Pro

KRN304-4

1         5
Ala—Glu—Ile—Thr—Arg—Ile

These results indicate that the prochymosinrelated species secreted by KRN303-1 has undergone no processing of the amino-terminal spacer sequence, while the species secreted from KRN304-4 has the authentic mature prochymosin amino terminus.

The following organisms were deposited with the American Type Culture Collection on June 30, 1987: HB101 pAB307, ATCC Accession No. 67454: HB101 pAB312, ATCC Accession No. 67455.

Although the foregoing invention has been described in some detail by way of illustration and example for purposes of clarity of understanding, it will be obvious that certain changes and modifications may be practiced within the scope of the appended claims.

We claim:

1. A DNA construct encoding a protein having an amino acid sequence which comprises a secretion-directing Kluyveromyces α-factor leader sequence linked to a heterologous polypeptide sequence.

2. The DNA construct according to claim 1, wherein said protein further comprises a yeast processing signal for processing said protein into said heterologous polypeptide between said leader sequence and said heterologous polypeptide sequence.

3. The DNA construct according to claim 1, further comprising a yeast promoter linked to the 5' end of said leader sequence.

4. The DNA construct according to claim 1, wherein said leader sequence is a Kluyveromyces lactis α-factor leader sequence.

5. The DNA construct according to claim 2, wherein said yeast processing signal comprises a basic dipeptide cleavage site and a spacer.

6. The DNA construct according to claim 5, wherein said basic dipeptide comprises at least one arginine.

7. The DNA construct according to claim 6, wherein said basic dipeptide is lysine-arginine or arginine-arginine.

* * * * *